(12) United States Patent
Gafney

(10) Patent No.: US 8,992,738 B2
(45) Date of Patent: Mar. 31, 2015

(54) METHOD FOR CONVERSION OF CARBON DIOXIDE TO METHANE USING VISIBLE AND NEAR INFRA-RED LIGHT

(75) Inventor: Harry D. Gafney, Muttontown, NY (US)

(73) Assignee: Research Foundation of the City University of New York, New York, NY (US)

( * ) Notice: Subject to any disclaimer, the term of this patent is extended or adjusted under 35 U.S.C. 154(b) by 218 days.

(21) Appl. No.: 13/391,202

(22) PCT Filed: Aug. 20, 2010

(86) PCT No.: PCT/US2010/046212
§ 371 (c)(1),
(2), (4) Date: Apr. 30, 2012

(87) PCT Pub. No.: WO2011/022683
PCT Pub. Date: Feb. 24, 2011

(65) Prior Publication Data
US 2012/0208903 A1 Aug. 16, 2012

Related U.S. Application Data

(60) Provisional application No. 61/235,566, filed on Aug. 20, 2009.

(51) Int. Cl.
*B01J 19/12* (2006.01)
*C07C 1/12* (2006.01)

(52) U.S. Cl.
CPC ................. *C07C 1/12* (2013.01); *B01J 19/127* (2013.01); *B01J 19/128* (2013.01); *C07C 2521/06* (2013.01); *C07C 2523/06* (2013.01); *C07C 2523/20* (2013.01); *C07C 2523/22* (2013.01); *C07C 2523/28* (2013.01);
(Continued)

(58) Field of Classification Search
CPC ......... B01J 19/127; B01J 19/128; C07C 1/12; C07C 2521/06; C07C 2523/06; C07C 2523/20; C07C 2523/22; C07C 2523/28; C07C 2523/30; C07C 2523/745; C07C 2531/22
USPC ..................................... 204/157.15; 205/340
See application file for complete search history.

(56) References Cited

U.S. PATENT DOCUMENTS 4,403,031 A * 9/1983 Borrelli et al. ................. 430/332
5,308,454 A * 5/1994 Anderson ................ 204/157.15
(Continued)

OTHER PUBLICATIONS

Look et al, "Formation of tungsten oxide and photocatalytic production of methane," Poster Abstracts, The 238th ACS National Meeting, Washington, DC, Aug. 16-20, 2009.*
(Continued)

*Primary Examiner* — Colleen M Raphael
(74) *Attorney, Agent, or Firm* — Hoffmann & Baron, LLP

(57) ABSTRACT

The invention relates to a method for converting carbon dioxide to methane. The method comprises exposing carbon dioxide adsorbed on a nanoporous silicate matrix to light in the presence of a source of carbon dioxide and a source of hydrogen for a time and under conditions sufficient to convert carbon dioxide to methane. The matrix contains at least one photochromic metal oxide entity, and contains a $C_1$ impurity site. The light has a wavelength of about 437 nm to about 1200 nm.

14 Claims, 4 Drawing Sheets

(52) U.S. Cl.
CPC ...... *C07C 2523/30* (2013.01); *C07C 2523/745* (2013.01); *C07C 2531/22* (2013.01)
USPC .................................................. 204/157.15

(56) References Cited

U.S. PATENT DOCUMENTS 5,888,425 A * 3/1999 Schwertfeger et al. ....... 427/220
2008/0119352 A1* 5/2008 Kitaguchi ...................... 502/74

OTHER PUBLICATIONS

Gafney et al, "Photocatalyzed conversion of CO2 to CH4," Proceedings of the Symposium on Environmental Aspects of Electrochemistry and Photoelectrochemistry, Tomkiewicz et al. eds, vol. 93-18, pp. 38-46.*

Higashimoto et al, "Photo-electrochemical properties of amorphous WO3 supported on TiO2 hybrid catalysis," Catalysis Letters vol. 101, Nos. 1-2, May 2005, pp. 49-51.*

Lin et al, "Photochemical CO2 Splitting by Metal-to-Metal Charge-Transfer Excitation in Mesoporous ZrCu(I)-MCM-41 Silicate Sieve," J. Am. Chem. Soc. 2005, vol. 127, pp. 1610-1611.*

* cited by examiner

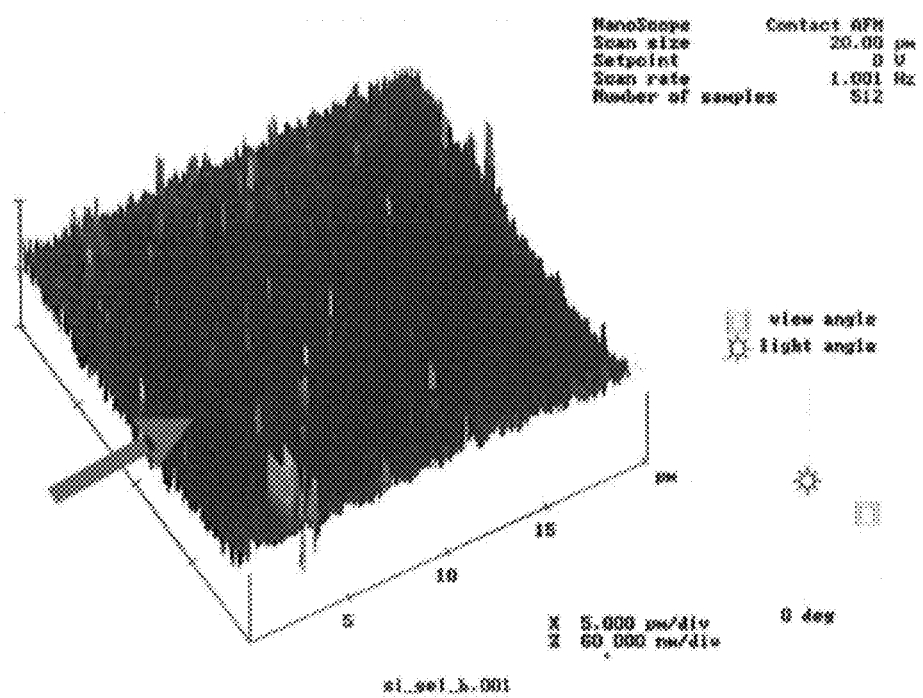
Figure 4. Crater (arrow) formed by the desorption of gaseous decomposition products during heating of TMOS/MeOH/H2O xerogel

METHOD FOR CONVERSION OF CARBON DIOXIDE TO METHANE USING VISIBLE AND NEAR INFRA-RED LIGHT

CROSS-REFERENCE TO RELATED APPLICATION

This application claims the benefit of U.S. Provisional Application No. 61/235,566, filed Aug. 20, 2009, which is incorporated herein by reference in its entirety.

TECHNICAL FIELD

The present invention generally relates to a method for conversion of carbon dioxide to methane through a photocatalytic process. The method uses visible and near infra-red light as a source of energy. This technology increases energy output and decreases greenhouse gas emissions by being able to use solar energy to convert carbon dioxide to methane.

BACKGROUND OF THE INVENTION

Combustion of methane releases a significant amount of energy, but occurs with the concurrent evolution of one mole of the greenhouse gas $CO_2$.

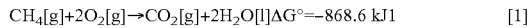

$$CH_4[g]+2O_2[g] \rightarrow CO_2[g]+2H_2O[l] \Delta G° = -868.6 \text{ kJ1} \quad [1]$$

A catalytic system utilizing ultraviolet light to recycle $CO_2$ to methane increases energy production and reduces greenhouse gas emission. Cycling the system n times releases n(868.6 kJ), but evolves only one mole of $CO_2$. (Olah et al., *J. Org. Chem.* (2009) 74(2):487-498; Haines, A., *Medicine, Conflict, and Survival* (2001) 17(1):56-62; Piver W., *Environmental Health Perspectives* (1991) 96:131-7; MacDonald, G. J., "The Long-Term Effects of Increasing Carbon Dioxide Levels," Ballinger, Cambridge, Mass., 1982; Nguyen et al., *Applied Catalysis A: General* (2008) 335:112-120; Lo et al., *Solar Energy Materials & Solar Cells* (2007) 91:1765-1774; Edmonds et al., *Greenhouse Gas Control Technologies, Proceedings of the International Conference on Greenhouse Gas Control Technologies, 6th*, Kyoto, Japan, 2002, pp. 1427-1432; Haneda et al., *Chemistry Letters* (2008) 37(8):830-831; Yan et al., *ACS Symposium Series* 2003, 852 (Utilization of Greenhouse Gases) pp. 42-56; Lo et al., *Zhongguo Huanjing Gongcheng Xuekan* (2005) 15(3):143-152; Pinaeva et al., "Environmental Challenges and Greenhouse Gas Control for Fossil Fuel Utilization in the 21st Century," "Environmental Challenges for Fossil Fuel Combustion"; "Greenhouse Gas Control and Utilization" American Chemical Society National Meeting, San Diego, Calif., 2001; Tan et al., *Catalysis Today* (2006) 115:269-273; Centi et al., *Applied Catalysis, B: Environmental* (2003) 41(1-2):143-155; Ziessel, R. "Carbon Dioxide as a Source of Carbon: Biochemical and Chemical Uses," Aresta et al., eds. Reidel, 1987, p 113; Dey, G. R. *Journal of Natural Gas Chemistry* (2007) 16(3):217-226; Iijima et al., *Mitsubishi Juko Giho* (2002) 39(5):286-289.)

Reduction of $CO_2$ to $CH_4$, formally an eight-electron process, is known to occur thermally and photochemically with ultraviolet light on silica surfaces doped with transition metal carbonyls. (Gafney, H. D., "Photochemistry of Metal Carbonyls Physisorbed on Porous Vycor Glass" in "Photochemistry on Solid Surfaces" Matsuura et al., eds., Elsevier, Amsterdam, 1989, 272; Gafney et al., *Inorg. Chem.* (1988) 27:2815; Gafney et al., "Photosensitive Metal-Organic Systems: Mechanistic Principles and Recent Applications", Kutal et al., eds. American Chemical Society (1993) p. 67; Brenner et al., *Inorg. Chem.* (1979) 18:1478-84; Brenner et al., *J. Am. Chem. Soc.* (1980) 102:2484-87; Simon et al., *Inorg. Chem.* (1988) 27:2733; Xu et al., *Proc. Electrochem. Soc.* (1993) 93-18, 38.)

The thermal reaction is stoichiometric, and requires high temperatures; $CH_4$ evolution is attributed to the hydrogenation of the coordinated carbonyl. The photochemical conversion is photocatalytic, occurs at room temperature and catalytically converts atmospheric $CO_2$ to $CH_4$ with co-adsorbed water providing hydrogen and the reducing equivalents. (Simon, R. C. "A Study of the Photochemistry and Photocatalysis of Group VIB Hexacarbonlys adsorbed to A Porous Glass Matrix", Ph.D. Thesis, City University of New York, 1983.)

For example, a 310-nm photolysis of $W(CO)_6$ physisorbed onto Corning's code 7930 porous Vycor glass (PVG) or tetramethoxysilane/methanol/water (TMOS/$CH_3OH/H_2O$) xerogels leads to $CH_4$ evolution. Photolysis initiates CO loss with the pentacarbonyl coordinating to a surface silanol group to form $W(CO)_5(OSi)$. (Simon et al., *Inorg. Chem.* (1985) 24:2565.) Continued photolysis leads to further CO loss, but when the complex is unable to achieve stability through coordination to the surface silanols, i.e., at an average stoichiometry of $W(CO)_4$, the chemistry changes and the complex undergoes oxidation with the concurrent evolution of CO, $H_2$ and $CH_4$. (Simon, R. C. "A Study of the Photochemistry and Photocatalysis of Group VIB Adsorbed to a Porous Glass Matrix", Ph.D. Thesis, CUNY, 1983: 94-103.)

There remains a need in the art for a method by which to convert carbon dioxide to methane which does not require high temperatures or a particular kind of light, but instead can be effected under more natural environmental conditions.

BRIEF DESCRIPTION OF DRAWINGS

FIG. 4 shows crater (arrow) formed by the desorption of gaseous decomposition products during heating of TMOS/$CH_3OH$/water xerogel.

SUMMARY OF THE INVENTION

Figure 1:
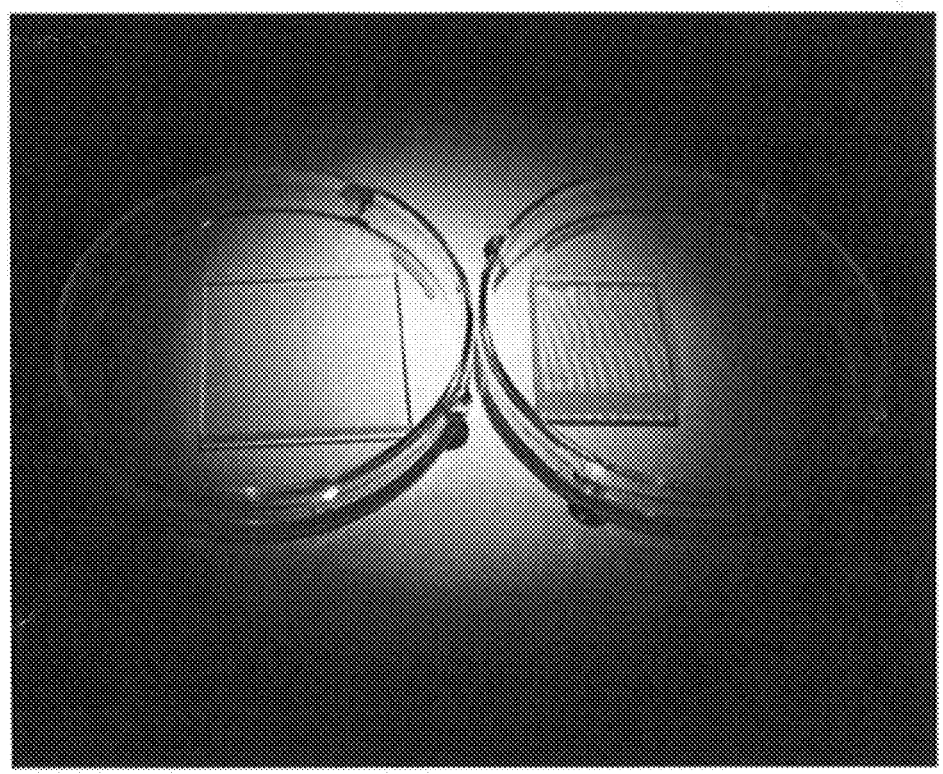
FIG. 1 shows polished (left) and unpolished or "rolled" (right) code 7930 porous Vycor glass.

In one embodiment, the invention relates to a method for converting carbon dioxide to methane. The method comprises exposing carbon dioxide adsorbed on a nanoporous silicate matrix to light in the presence of a source of carbon dioxide and a source of hydrogen for a time and under conditions sufficient to convert carbon dioxide to methane. The matrix contains at least one photocatalyst, and contains a $C_1$ impurity site. The light has a wavelength of about 437 nm to about 1200 nm.

The photocatalyst can be a photochromic metal oxide entity, a bimetallic coordination complex, or mixtures thereof. A photochromic metal oxide entity can be a photochromic transition metal oxide or bronze.

Typically, the photochromic transition metal oxide is $W_3O_8$, ranging in various stoichiometric forms of up to $W_{75}O_{200}$; $Mo_3O_8$, ranging in various stoichiometric forms of up to $Mo_{75}O_{200}$; $Fe_3O_4$, ranging in various stoichiometric forms of up to $Fe_{75}O_{100}$; $Ti_3O_2$, ranging in various stoichiometric forms of up to $Ti_{75}O_{50}$; $V_3O_7$, ranging in various stoichiometric forms of up to $V_{75}O_{175}$; $Nb_3O_3$, ranging in various stoichiometric forms of up to $Nb_{75}O_{75}$, or mixtures thereof.

Typically, the photochromic bronze is $W_3O_9H_2$, ranging in various stoichiometric forms of up to $W_{75}O_{201}H_2$; $Mo_3O_9H_2$, ranging in various stoichiometric forms of up to $Mo_{75}O_{201}H_2$; $Fe_3O_5H_2$, ranging in various stoichiometric forms of up to $Fe_{75}O_{101}H_2$; $Ti_3O_3H_2$, ranging in various stoichiometric forms of up to $Ti_{75}O_{51}H_2$; $V_3O_8H_2$, ranging in various stoichiometric forms of up to $V_{75}O_{176}H_2$; $Nb_3O_4H_2$, ranging in various stoichiometric forms of up to $Nb_{75}O_{76}H_2$; or mixtures thereof.

Typically, the bimetallic coordination complex is [(bis-2, 2'-bipyridiyl)M(2,3 dipyridylpyrazine)XO$_3$]$^{2+}$, wherein M is Ru or OS, and X is W or M; or mixtures thereof.

DETAILED DESCRIPTION OF THE INVENTION

The present invention relates to methods of converting carbon dioxide to methane. The methods comprise exposing carbon dioxide adsorbed on a nanoporous silicate matrix to light in the presence of a source of carbon dioxide and a source of hydrogen for a time and under conditions sufficient to convert carbon dioxide to methane.

The light has a wavelength in the range of about 437 nm to about 1200 nm, more typically, in the range of about 437 nm to about 1000 nm. Solar energy, e.g., sunlight, is preferred.

In one embodiment, the nanoporous silicate matrix contains at least one type of photochromic metal oxide entity. Electronic adsorption spectra indicate that the metal oxide entity is photochromic where the metal is present as a mixture of different oxidation states (i.e., different valencies). In another embodiment, instead of photochromic metal oxide entities, the nanoporous silicate matrix contains at least one type of a bimetallic coordination complex.

Photochromic Metal Oxide Entity

Examples of photochromic metal oxide entities include photochromic transition metal oxides; photochromic bronzes; and mixtures thereof. A mixture of different photochromic metal oxide entities can be used in the methods. Typically, one type of photochromic metal oxide entity is used.

Photochromic transition metal oxides have the general formula of $M_xO_y$, wherein M is a transition metal, and wherein $x \leq 100$ and $y \leq 300$, where the metals exist in different oxidation states. Typical examples of M include titanium, tungsten, molybdenum, iron, vanadium, niobium, and zinc.

Typical examples of $M_xO_y$ include $W_3O_8$, ranging in various stoichiometric forms of up to $W_{75}O_{200}$; $Mo_3O_8$, ranging in various stoichiometric forms of up to $Mo_{75}O_{200}$; $Fe_3O_4$, ranging in various stoichiometric forms of up to $Fe_{75}O_{100}$; $Ti_3O_2$, ranging in various stoichiometric forms of up to $Ti_{75}O_{50}$; $V_3O_7$, ranging in various stoichiometric forms of up to $V_{75}O_{175}$; and $Nb_3O_3$, ranging in various stoichiometric forms of up to $Nb_{75}O_{75}$.

Photochromic bronzes have the general formula of $M_xO_{y+1}A_2$, wherein M is a transition metal, wherein $x \leq 100$ and $y \leq 300$, and wherein A is H, Li, Na, K, Rb, Cs or Fr. Typical examples of M include titanium, tungsten, molybdenum, iron, vanadium, niobium, and zinc.

Typical examples of $M_xO_{y+1}A_2$ include $W_3O_9H_2$, ranging in various stoichiometric forms of up to $W_{75}O_{201}H_2$; $Mo_3O_9H_2$, ranging in various stoichiometric forms of up to $Mo_{75}O_{201}H_2$; $Fe_3O_5H_2$, ranging in various stoichiometric forms of up to $Fe_{75}O_{101}H_2$; $Ti_3O_3H_2$, ranging in various stoichiometric forms of up to $Ti_{75}O_{51}H_2$; $V_3O_8H_2$, ranging in various stoichiometric forms of up to $V_{75}O_{176}H_2$; and $Nb_3O_4H_2$, ranging in various stoichiometric forms of up to $Nb_{75}O_{76}H_2$.

A matrix containing photochromic metal oxide entities is provided, or is formed. Typically, the photochromic metal oxide entity is formed in situ, i.e., in or on the matrix. For example, at least one monometallic carbonyl precursor of a photochromic metal oxide entity is physioadsorbed on the matrix surface. Examples of monometallic carbonyl precursors include $W(CO)_6$, $Mo(CO)_6$, and $Fe_3(CO)_{12}$.

To form the photochromic transition metal oxides, the precursor on the matrix may be exposed to ultraviolet light. To form the photochromic bronzes, the matrix is slightly acidic, i.e., at a pH of about 2-5, when exposed to the ultraviolet light. Time of exposure to ultraviolet light varies depending upon initial loading of precursor, the correlation length of the matrix, and the ultraviolet excitation intensity. Typically, the exposure is from about one minute to about fifteen minutes to about thirty minutes.

Typically, the precursors are loaded onto a matrix so that about $10^{-6}$ to about $10^{-4}$ moles of precursor are present per gram of the matrix. Different loadings are required for different precursors depending on the correlation length of the matrix, excitation intensity, and the quantum efficiency of degradation of the precursor. For example, because the correlation length of a xerogel is shorter, higher loadings are needed for the xerogel than for the PVG. The excitation intensity ranges from about $4.65 \times 10^{-4}$ joules/cm$^2$-sec to about $4.65 \times 10^{-1}$ joules/cm$^2$-sec.

Bimetallic Coordination Complexes

In another embodiment, instead of photochromic metal oxide entities, the nanoporous silicate matrix contains at least one type of a bimetallic coordination complex.

A bimetallic coordination complex is composed of a photoactive electron transfer agent and a photocatalytic metal oxide. These complexes absorb in visible light. Examples of these complexes include Ru(II) diimine-metal oxide polymetallics; and Os(II) diimine-metal oxide polymetallics. More specific examples include [(bis-2,2'-bipyridiyl)M(2,3 dipyridylpyrazine)XO$_3$]$^{2+}$, wherein M is Ru or Os, and X is W or Mo.

In this embodiment, a bimetallic coordination complex is loaded onto the matrix (i.e., not a precursor). Typically, the complex are loaded onto a matrix so that about $10^{-6}$ to about $10^{-5}$ moles of complex are present per gram of the matrix.

Nanoporous Silicate Matrices

The nanoporous silicate matrix suitable for the methods of the invention has spinodal structures with intervening spaces defining an interconnected pore structure randomly dispersed throughout the matrix. Typically, the matrix contains a hydroxylated surface with free and associated Si—OH groups.

The nanoporous silicate matrix of the present invention contains at least one carbonaceous impurity site on its surface, referred to in the art as a "$C_1$ impurity site." The $C_1$ impurity site is a site where a carbon atom is chemisorbed. Any carbon atoms initially on the matrix are depleted during the course of the conversion methods of the present invention, and replenished by the source of carbon dioxide. Thus, the matrix provides a $CO_2$ adsorption site.

The correlation length of a suitable matrix is such that it allows the rate of aggregation of a metal oxide entity to compete with its rate of oxidation. Without wanting to be held to a mechanism, it is believed that such a condition allows for the metal of a metal oxide entity to exist in multiple oxidation states thereby yielding photochromic metal oxide entities. The correlation length is the length of uniform density and is thought to define the region over which metal aggregation occurs. Since aggregation is in competition with oxidation, the correlation length is thought to be the principal determinant for the formation of the photochromic metal oxide entities. The loading (i.e., amount) of precursor required to form photochromic metal oxide entities is inversely proportional to the correlation length of the matrix being used.

An example of a suitable nanoporous silicate matrix is unpolished, rolled glass. A more specific example is unpolished Corning code 7930 porous Vycor glass (i.e., PVG). The characteristic correlation length for PVG is about 22±1 nm.

Another example of a suitable nanoporous silicate matrix is tetramethoxy-silane/methanol/water xerogel (i.e., TMOS/$CH_3OH$/water xerogel). The TMOS/$CH_3OH$/water xerogel is dried so that its spinodal structures remain intact. The xerogel is typically slow dried at about 150° C. to about 500° C., more typically at about 180° C. to about 200° C. The TMOS/$CH_3OH$/water xerogel is typically base-catalyzed with ammonia. The characteristic correlation length for the xerogel is about ≤1 nm.

Reduction of $CO_2$ to $CH_4$ occurs photocatalytically in the nanoporous silica matrices containing the photochromic metal oxide entity or bimetallic coordination complex. $CH_4$ evolution occurs from polished and rolled PVG, and dried TMOS/$CH_3OH$/$H_2O$ xerogels.

The excitation intensity ranges from about $4.65 \times 10^{-4}$ joules/$cm^2$-sec to about $4.65 \times 10^{-1}$ joules/$cm^2$-sec. The excitation intensity is the energy flux required to effect the conversion from carbon dioxide to methane.

Source of Hydrogen

The source of hydrogen for the methods of the present invention can be any suitable source of hydrogen. A preferred source of hydrogen is water. Water is naturally present on the matrices. However, once the naturally-occurring water is depleted, water can be added.

Hydrogen can also be supplied as hydrogen gas. For example, a source is hydrogen derived from the water-gas shift reaction (i.e., $CO + H_2O \rightarrow CO_2 + H_2$).

Source of Carbon Dioxide

The source of carbon dioxide for the methods of the present invention can be any suitable source of carbon dioxide. A preferred source of carbon dioxide is ambient environmental carbon dioxide. Another example of a source is carbon dioxide derived from the exhaust of an industrial reaction or operation.

In another embodiment, this application describes a photocatalytic system composed of photochromic $TiO_2$, $WO_3$, $MoO_3$, $Fe_2O_3$, and mixtures of these metal oxides adsorbed onto nanoporous silicas that adsorb $CO_2$, and using visible light as the energy source and water as the source of reducing equivalents and protons, converts the adsorbed $CO_2$ to methane, $CH_4$.

In this embodiment, a method for conversion of carbon dioxide to methane using a system composed of at least one photochromic transition metal oxide catalyst doped onto nanoporous silica and using visible light as the energy source is provided.

Figure 2:
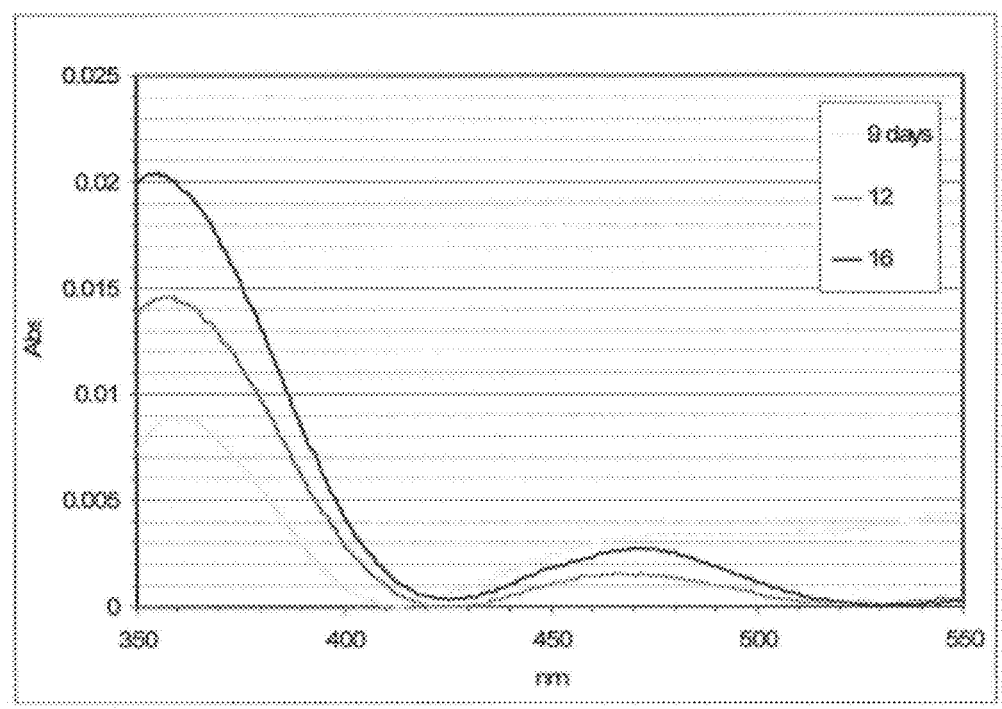
FIG. 2 indicates absorption of UV-visible spectra after 312 nm photolysis and heating at 625° C. for 9, 12 and 16 days of non-photochromic metal carbonyls.
Figure 3:
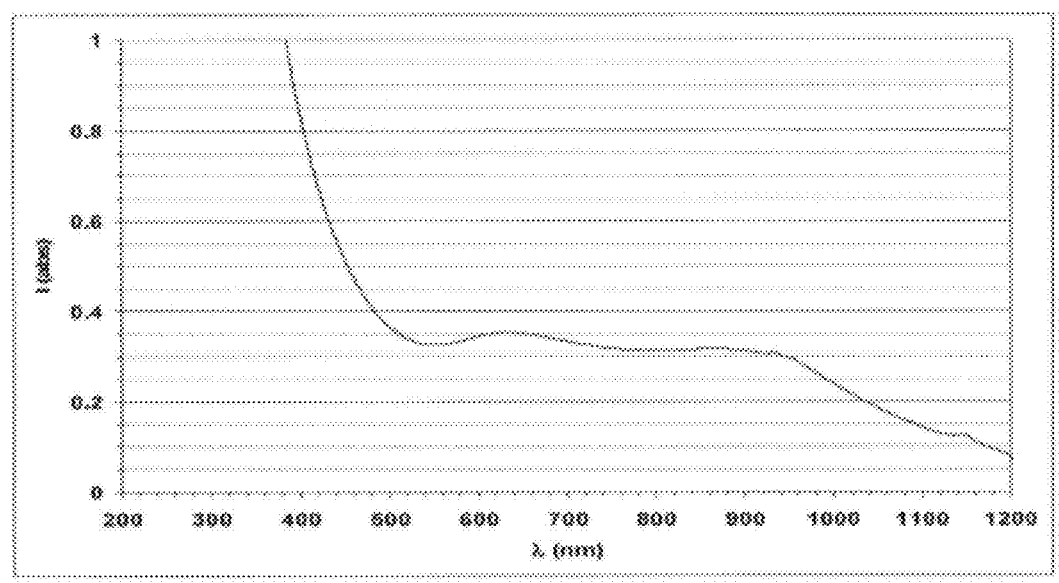
FIG. 3 indicates absorption of UV-visible spectrum after photolysis of $W(CO)_6$ in "rolled" PVG.

Conversion of $CO_2$ to $CH_4$ at or near 0V implies that it is possible to drive the conversion with visible and near-IR light. The difficulty is that the known photocatalyst, the oxides of Ti, W, Mo and Fe, absorb in the UV and do not absorb visible light (refer to FIG. 2). Previous applications, for example, report that the conversion is driven by UV light, <350-nm, which the photocatalytic oxides adsorb. It has now been discovered that the photochromic forms of photocatalytic oxides, which absorb visible and near-IR light, photocatalyze the conversion. Photochromic $WO_3$, for example, is dark blue with spectral features extending throughout the visible and into the near-IR (refer to FIG. 3).

Experiments confirm that excitation of PVG and TMOS/$CH_3OH$/$H_2O$ xerogel impregnated with photochromic $WO_3$ with light of >430 nm, i.e., visible and near-IR light, converts $CO_2$ to $CH_4$. The available data indicate that the mechanism of conversion, whether driven by UV or visible light is the same—adsorption of $CO_2$ onto sites in the silica matrix and the photoexcited, photochromic metal oxide promoting the transfer of reducing equivalents and protons thereby converting the adsorbed carbon dioxide to methane. Furthermore, the photocatalytic, photochromic oxides can be formed in situ in these nanoporous silica matrices from readily available monometallic precursors. And in view of the minimal energy requirements, 0V, more than likely, the conversion can be driven by all known photochromic transition metal oxides.

Transition metal oxides like $Fe_2O_3$, $MoO_3$, and tungston oxide may be used as suitable catalysts. The transition metal oxides may be used individually or in mixtures. The transition metal oxides may be doped with other metal oxides like $TiO_2$.

EXAMPLES

Materials: Porous Silica Matrices

Although obtained by different procedures, Corning code 7930 porous Vycor glass (PVG) and dried (200° C.), base-catalyzed ($NH_3$) tetramethoxysilane/methanol/water (TMOS/$CH_3OH$/$H_2O$) xerogels are structurally and chemically similar materials. (Iler, R. K., "The Chemistry of Silica", Wiley-Interscience, New York, 1979, p 3; Scholz, H. in "Glass: Nature, Structure and Properties," Springer, New York, 1991; Enke et al., *Microporous and Mesoporous Materials* (2003) 60(1-3):19-30; Janowski et al., *Z Chem.* (1989) 19, 1; Janowski et al., *Handbook of Porous Solids* (2002) 3:1432-1542; Enke et al., *Colloids and Surfaces, A: Physicochemical and Engineering Aspects* (2001) 187-188:131-139; Brinker et al., "Sol-Gel Science The Physics and Chemistry of Sol-Gel Processing," Academic Press, New York, 1989, pp. 471, 515-610; Dong, J. "Fabrication and Characterization of Porous Glass Derived Optical Materials and Devices" Ph.D. Thesis, CUNY, 1997, pps. 156-160.)

PVG derives from a 96% $SiO_2$, 3% $B_2O_3$ and 1% $Na_2O$ and $Al_2O_3$ melt. The borate phase separates on cooling and, this phase being readily soluble in dilute nitric acid, the leaching of that phase yields transparent (50% T at 259 nm vs air), spinodal structures with the intervening spaces defining an interconnected pore structure randomly dispersed throughout the glass. Base-catalyzed ($NH_3$) gelation of a TMOS/MeOH/$H_2O$ solution at room temperature followed by slow drying at room temperature under reduced pressure and then at 200° C. produces a transparent (50% T at 390 nm vs. air) structurally similar nodular, glass-like material with the intervening spaces defining an interconnected, randomly dispersed porosity throughout the material. Table I summarizes the structural parameters of both matrices.

TABLE I

Structural Parameters of PVG and TMOS/MeOH/H$_2$O Xerogels

|  | Surface Area | Pore Size | Surface Irregularity | Silica Nodule Diameter | Correlation Length | Surface Features & Size |
|---|---|---|---|---|---|---|
| PVG | 183 ± 15 m$^2$/g | 9 ± 2 nm | ±440 nm | 3-5 μm | 22 ± 1 nm | Stalagmites 30 ± 10 nm high; 30 ± 10 nm Wide |
| Xerogel | 508 ± 18 m$^2$/g | 0.5-2000 nm | ±286 nm | 2-4 μm | ≤1 nm[i] | Stalagmites 1-2 nm high 1-3 nm wide |

[i](a) Woignier, T.; Phalippou, J.; Vacger, R.; "Better Ceramics Through Chemistry II", Brinker, C. J.; Clark, D. E.; Ulrich, D. R. Eds., *Mater. Res. Soc.* 1986, p. 57. (b) Himmel, B.; Gerber, T.; Buerger, H. *J. Non-Crystal. Solids*, 1987, 91(1), 122-36. (c) Brinker, C. J.; Keefer, K. D.; Schaefer, D. W.; Assink, R. A.; Kay, B. D.; Ashley, C. S. *J. Non-Crystal. Solids*, 1984, 63(1-2), 45-59. (d) Schaefer, D. W.; Keefer, K. D.; Brinker, C. J., *Polymer Preprints* (ACS) 1983, 24(2), 239-40.

Both materials possess hydroxylated surfaces with free or isolated and associated or H-bonded Si—OH groups. (Gafney et al., *Comments on Inorg. Chem.* (2003) 24(3-4): 69-136.) In dried (500° C.) PVG, the free silanols exhibit a sharp band at 3755 cm$^{-1}$ with the associated or hydrogen bonded silanols appearing as a distinct shoulder at 3650 cm$^{-1}$. The free silanol band in a dried (200° C.) TMOS/MeOH/H$_2$O xerogel appears at 3744 cm$^{-1}$ with the associated silanols appearing as a shoulder at 3650 cm$^{-1}$ along with bands at 2959 and 2852 cm$^{-1}$ due to OCH$_3$ functionalities within the xerogel. The relative intensities of the 3650 cm$^{-1}$ bands, normalized to the intensity of the free silanol band, suggests the ratio of free to associated silanols is not that different in the two matrices. The xerogel exhibits a slightly stronger, broad absorption centered at 3450 cm$^{-1}$, however, implying that the xerogel, although dried at 200° C. for as long as a month, probably possess more chemisorbed water.

The 3-5-μm diameter nodules in PVG are aggregates of smaller, 300-600 nm diameter SiO$_2$ nodules with the surfaces of these nodules covered by sharp stalagmite-like features with an average height of 40±20 nm and average width of 40±20 nm. The PVG surface is characterized by an irregularity, i.e., a deviation from a hypothetical flat plane, of ±440 nm. N$_2$ adsorption-desorption measurements yield a type H2 isotherm (IUPAC classification). The surface area calculated from the N$_2$ adsorption isotherm, 184±10 m$^2$/g of PVG, is within experimental error of previous measurements, while desorption isotherms yield pore diameters of 9±2 nm.

The (TMOS/CH$_3$OH/H$_2$O) xerogels possess a similar structural motif of 5-8 μm diameter silica nodules which are aggregates of 70 to 200-nm diameter SiO$_2$ nodules. Stalagmite-like features are also present on the surfaces of these smaller nodules, although the number and size, 5 to 20 nm wide and 10 to 20 nm high, are smaller than those on PVG. The xerogel surfaces are characterized by an irregularity of ±286 nm. N$_2$ adsorption-desorption isotherms (IUPAC classification Type H1) differ from those obtained with PVG. Surface areas fall within the 500-600 m$^2$/g range while the desorption isotherm yields a range of pore diameters ranging from 0.5 nm to 1-2 μm.

Water is ubiquitous in both materials and its desorption occurs over a wide temperature range. Weight losses in 80-150° C. range are due to desorption of physisorbed water from PVG, and physisorbed water and methanol from the xerogels. These are followed by a continued decline in sample weight at a reduced rate with a marked increase in weight loss beginning at ca. 500° C. in the xerogel and 600° C. in PVG due to the loss of chemisorbed water and water derived from silanol condensation to form a consolidated glass. Slight structural contractions of both matrices accompany desorption of physisorbed water, although the contractions do not change the surface area of either matrix beyond experimental error. The surface area of PVG changes little up to 600° C. and then declines smoothly with the steepest decline in the 900-1000° C. region. The surface area of the xerogel (508±18 m$^2$/g at room temperature for the xerogel in FIG. 4) changes little up to 300° C., but then begins to oscillate showing both increases and decreases in the 300 to 500° C. range followed by a decline in the 500-800° C. range. The oscillations arise from the thermal decomposition of the Si—OCH$_3$ groups and the subsequent desorption of the decomposition products from the consolidating matrix. Decomposition and desorption are violent, exothermic processes leading to the formation of numerous sharp-edged craters (FIG. 4, arrow) on the xerogel surface. In xerogels containing Fe$_2$O$_3$, the conversion of the octahedrally coordinated Fe$^{3+}$ to tetrahedrally coordinated Fe$^{3+}$ coincides with the appearance of these craters. The absence of an O$_h$-T$_d$ conversion in PVG containing Fe$_2$O$_3$, where consolidation occurs without a chaotic domain or crater formation, suggests desorption of the Si—OCH$_3$ decomposition products disrupts the forming Si—O network creating tetrahedral Si vacancies into which Fe$^{3+}$ incorporates.

Beyond this chaotic domain, consolidation of the xerogel parallels that of PVG, but at slightly lower temperatures. The glass transition temperature of PVG is 848±20° C., while viscous sintering occurs at 1105±18° C. An exothermic process at 1120° C. is also attributed to the viscous sintering of the SiO$_2$ glass derived from the xerogel. Since the desorption processes occur prior to the onset of xerogel consolidation, they can be a way to increase the number of CO$_2$ adsorption-activating sites.

Formation of photochromic tungsten or molybdenum oxide and/or bronze from the zero-valent, monometallic hexacarbonyl require oxidation and aggregation. Since aggregation is a function of the correlation lengths of these nanoporous silica matrices, the differences in the correlation lengths of the two matrices (Table I) and MCM-41 is exploited in conjunction with initial loading, light intensity and water and oxygen contents to influence photochromic formation.

Silicate Morphology. Although chemically and structurally similar, PVG and dried TMOS/MeOH/H$_2$O xerogels are fundamentally different materials. PVG is an acid-leached, nanoporous glass, whereas the dried (≤200° C.) TMOS/MeOH/H$_2$O xerogel is a partially polymerized silica. PVG also possesses borate Lewis acid sites, whereas the xerogels do not. The evolution of CH$_4$ after tying up the borate Lewis acid sites with NH$_3$, and its evolution from WO$_3$ or W(CO)$_6$ impregnated TMOS/MeOH/H$_2$O xerogels, which do not contain borates, establishes that the borate Lewis acid sites in PVG are not necessary for the photocatalyzed conversion of CO$_2$ to CH$_4$.

The original CH$_4$ evolution experiments were carried out on unpolished or "rolled" PVG (FIG. 1). "Rolled" refers to the glass as it comes from the mill and is then leached in dilute HNO$_3$. To improve the spectral precision by minimizing scattering from the rippled surface of the rolled glass, a switch to polished PVG was made (FIG. 1). Initial experiments with the doped, polished samples, however, failed to evolve methane, or produced little more than a trace of CH$_4$. Chemical analyses and SEM analyses of the outer surface, the leach plane, and the structure intermediate between the two confirm both forms of the nanoporous silicate are chemically identical within experimental error, and structurally identical on a ≥50 nm length scale. CH$_4$ evolution has since been confirmed from both forms of PVG, but requires different loadings and excitation intensities. However, CH$_4$ evolution from the polished samples is consistently smaller than that from the "rolled" glass. Since CO$_2$ adsorbed into a depleted C$_1$ impurity site is converted to CH$_4$ and polishing removes the outer volumes of PVG, the majority of the "C$_1$ impurity sites" must be within the outer volumes of PVG. Two possibilities exist for the creation of these C$_1$ impurity sites; a reaction with atmospheric CO$_2$ as the melt is rolled into sheets, or during the leaching process. Current evidence points to a reaction with atmospheric CO$_2$ as the melt is rolled into sheets.

A major finding is the different chemistries of the oxide photoproducts in the two forms of PVG. In polished PVG, 312-nm photolysis of W(CO)$_6$(ads) yields monoclinic WO$_3$ which, consistent with a 2.6 eV band gap, absorbs in the UV. A 312-nm photolyses of W(CO)$_6$ads in the rolled glass, however, turns the glass dark blue. Electronic spectra, sensitivity to O$_2$, regeneration of blue by photolysis, and the product stability indicate formation of photochromic tungsten oxide, W$_y$O$_z$, or bronze, H$_x$W$_y$O$_z$. W(CO)$_6$ads absorbs in the UV and 312-nm excitation is needed to form the photochromic, but once formed visible light photolyses of the photochromic leads to CH$_4$ evolution. The lower energy transitions are assigned to intervalence, principally W$^{5+}$→W$^{6+}$, charge transfer or polaron absorptions, but CH$_4$ evolution occurs with no measurable decline in absorbance at 600 nm. In fact, cycling the sample shown through three photolysis, and CO$_2$ exposures slightly increased absorbance at 600 nm establishing that the photoreaction is not stoichiometric, but photocatalytic. Available data point to a mechanism equivalent to that with 312-nm excitation; reduction of a C$_1$ oxide impurity with coadsorbed water supplying the hydrogen and reducing equivalents, and replenishing the depleted site with CO$_2$ except that the photochromic photocatalyzes the conversion with visible light.

Possible Photocatalysis Mechanism

The photochemistry of the present invention is similar to the thermal activation of the complex on silica gel, where CH$_4$ evolution is attributed to the hydrogenation of the coordinated CO. But $^{13}$C labeling and quantitating the amounts of W($^{13}$CO)$_6$ reacted, and $^{12}$CO, $^{13}$CO, $^{12}$CH$_4$ and $^{13}$CH$_4$ evolved, establish the photochemically evolved methane does not derive from the coordinated CO (Gafney et al., Inorg. Chim. Acta, (1995) 40, 645). Rather, it derives from a carbonaceous impurity thought to be a "carbonate-like C$_1$ oxide" on the surfaces of the silica matrix (Xu, S. "Photocatalytic Behavior of Tungsten Carbonyl and Ruthenium Dodecacarbonyl Supported on Porous Glass", Ph.D. Thesis, CUNY 1994).

Consistent with an impurity, CH$_4$ evolution declines and eventually ceases during prolonged photolysis with the amount of CH$_4$ evolved never exceeding the reported C impurity level in PVG (Morse, D. L., Corning Glass Inc., private communication, 1984). Exposing the depleted sample to $^{13}$CO$_2$ (25-300 torr), however, leads to immediate $^{13}$CH$_4$ and $^{13}$CO evolution upon excitation establishing that CO$_2$ repopulates the carbonaceous impurity site and continued photolysis converts the adsorbed CO$_2$ to CH$_4$. The absence of CH$_4$ evolution during prolonged 254- or 310-nm photolysis of unimpregnated glasses, and its immediate appearance when a WO$_3$ impregnated sample is exposed to CO$_2$ and irradiated with 310-nm light, establishes that the silica matrix provides a CO$_2$ adsorption site, but excitation of the tungsten oxide photocatalytically converts the adsorbed CO$_2$ to CH$_4$.

Detection of formaldehyde and methanol intermediates indicates a sequence

$$CO_2 \to HCOOH \to HCOH \to H_3COH \to CH_4 \qquad [2]$$

similar to the Fischer-Tropsch hydrogenation of CO, except that the carbon being hydrogenated is not coordinated CO, but a "carbonate-like C$_1$ oxide" impurity in the glass matrix. Unlike the Fischer-Tropsch process, where the carbon content of the hydrocarbon is increased by successive additions of CO, the carbon content of the photochemically-evolved hydrocarbon is limited by the carbon content of the C$_1$ impurity, or as found, CH$_4$. With 310-nm excitation, the fraction of $^{13}$CO$_2$ converted to $^{13}$CH$_4$ ranges from 10 to 40% with turnover frequencies ranging from $0.3 \times 10^6$ s$^{-1}$ to $3.2 \times 10^6$ s$^{-1}$, and a quantum efficiency of methane evolution of 0.14±0.03. The latter is thought to be a lower limit since, at the loadings examined, the silica matrix in addition to the metal oxide absorbs the 312-nm excitation. The glass provides an adsorption site, but photoactivation of the metal oxide reduces CO$_2$ to CH$_4$.

Deuteration of 33-50% of the spectrally detectable Si—OH groups yields CH$_4$, CH$_3$D and small amounts of CH$_2$D$_2$. Although a high frequency shoulder on the 2760-cm1 SiO-D band indicates rapid proton exchange between chemisorbed D$_2$O and the silanol groups, CH$_4$ evolution is dependent on the amount of adsorbed water with $\Phi_{CH4}$ initially increasing with increasing adsorbed water, but eventually declining suggesting that, in excess, H$_2$O competes with CO$_2$ for adsorption onto the active site.

Photolysis under $^{13}$CO$_2$, yields $^{13}$CH$_4$, $^{13}$CO, H$_2$ and O$_2$ indicating the following reactions also occur

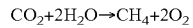
$$CO_2 + 2H_2O \to CH_4 + 2O_2 \qquad [3]$$

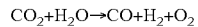
$$CO_2 + H_2O \to CO + H_2 + O_2 \qquad [4]$$

The amount of O$_2$ detected ranges from ca. 40 to 75% of the theoretical yield of 3 mol of O$_2$ per mol of CO and CH$_4$. The reason for the discrepancy is not clear, but H$_2$ evolution precedes CH$_4$ evolution, and the reaction stoichiometry may be biased by concurrent direct hydrogenation,

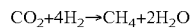
$$CO_2 + 4H_2 \to CH_4 + 2H_2O \qquad [5]$$

Collectively, the data point to CH$_4$ evolution occurring principally via reaction 2

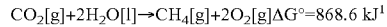
$$CO_2[g] + 2H_2O[l] \to CH_4[g] + 2O_2[g] \quad \Delta G° = 868.6 \text{ kJ}^1 \qquad [6]$$

with chemisorbed water providing the hydrogen and reducing equivalents.

A number of changes in the manufacturing of Corning's code 7930 glass have occurred since the original methane evolution experiments were carried out in the late seventies and early eighties. It is important to emphasize, however, that methane evolution has been confirmed from the older and the newer samples of the glass and has been confirmed from TMOS/CH$_3$OH/H$_2$O xerogels.

The sequence suggested by formaldehyde and methanol intermediates, reaction 2, corresponds to the overall reaction $$CO_2 + 8H^+ + 8e^- \rightarrow CH_4 + 2H_2O \quad E° = 0.169V \quad [7]$$

which, although exergonic under standard conditions, the energetics depend on acidity. Adsorption of colorimetric acid-base indicators onto PVG indicates a surface pH of 4 to 5 which make the reaction slightly endergonic, E=−0.07. The energetics improve with increasing acidity, and the Nernst equation predicts reaction 7 becomes exergonic at ca. pH=3. These are clearly approximations, but carrying out the conversion on glasses where the adsorption of colorimetric indicators indicate a surface pH of about 2 increases the CH$_4$ yield significantly relative to that on PVG. As Galus points out "in theory CO$_2$ as well as H$_2$CO$_3$ or carbonates may be further reduced to carbon or methane. The thermodynamic potential of these reactions are quite near 0V. However, due to large over potentials, these reactions were not observed in aqueous solution." (Galus, Z. in "Standard Potentials in Aqueous Solution" Bard, A. J.; Parsons, R.; Jordon, J., Eds., Marcel Dekker, New York, 1985, p. 195-197.)

The invention claimed is:

1. A method for converting carbon dioxide to methane, the method comprising exposing carbon dioxide adsorbed on a nanoporous silicate matrix to light in the presence of a source of carbon dioxide and a source of hydrogen for a time and under conditions sufficient to convert carbon dioxide to methane;
wherein the matrix contains at least one photochromic metal oxide entity, and contains a C$_1$ impurity site; and
wherein the light has a wavelength of about 437 nm to about 1200 nm.

2. The method according to claim 1, wherein the photochromic metal oxide entity is a photochromic transition metal oxide, a photochromic bronze, or mixtures thereof.

3. The method according to claim 2, wherein the photochromic transition metal oxide has the general formula of M$_x$O$_y$, wherein M is a transition metal present as a mixture of different oxidation states, and wherein x≤100 and y≤300.

4. The method according to claim 3, wherein M of the photochromic transition metal oxide is titanium, tungsten, molybdenum, iron, vanadium, niobium, zinc, or mixtures thereof.

5. The method according to claim 3, wherein the photochromic transition metal oxide is tungsten oxide, ranging in various stoichiometric forms from W$_3$O$_8$ to W$_{75}$O$_{200}$; molybdenum oxide, ranging in various stoichiometric forms from Mo$_3$O$_8$ to Mo$_{75}$O$_{200}$; iron oxide, ranging in various stoichiometric forms from Fe$_3$O$_4$ to Fe$_{750}$O$_{100}$;titanium oxide, ranging in various stoichiometric forms from Ti$_3$O$_2$ to Ti$_{75}$O$_{50}$; vanadium oxide, ranging in various stoichiometric forms from V$_3$O$_7$ to V$_{75}$O$_{175}$; niobium oxide, ranging in various stoichiometric forms from Nb$_3$O$_3$ to Nb$_{75}$O$_{75}$, or mixtures thereof.

6. The method according to claim 3, wherein the photochromic transition metal oxide is tungsten oxide, ranging in various stoichiometric forms from W$_3$O$_8$ to W$_{75}$O$_{200}$; or molybdenum oxide, ranging in various stoichiometric forms from MO$_3$O$_8$ to Mo$_{75}$O$_{200}$.

7. The method according to claim 2, wherein the photochromic bronze has the general formula of M$_x$O$_{y\pm 1}$A$_2$, wherein M is a transition metal present as a mixture of different oxidation states, wherein x≤100 and y≤300, and wherein A is H, Li, Na, K, Rb, Cs or Fr.

8. The method according to claim 7, wherein the M of the photochromic bronze is titanium, tungsten, molybdenum, iron, vanadium, niobium, zinc, or mixtures thereof.

9. The method according to claim 7, wherein the photochromic bronze is photochromic tungsten bronze, ranging in various stoichiometric forms from W$_3$O$_9$H$_2$ to W$_{75}$O$_{201}$H$_2$; photochromic molybdenum bronze, ranging in various stoichiometric forms from Mo$_3$O$_9$H$_2$ to Mo$_{75}$O$_{201}$H$_2$; photochromic iron bronze, ranging in various stoichiometric forms from Fe$_3$O$_5$H$_2$ to Fe$_{75}$O$_{101}$H$_2$; photochromic titanium bronze, ranging in various stoichiometric forms from Ti$_3$O$_3$H$_2$ to Ti$_{75}$O$_{51}$H$_2$; V$_3$O$_8$H$_2$, photochromic vanadium bronze, ranging in various stoichiometric forms from V$_3$O$_8$H$_2$ to V$_{75}$O$_{176}$H$_2$; Nb$_3$O$_4$H$_2$, photochromic niobium bronze, ranging in various stoichiometric forms from Nb$_3$O$_4$H$_2$ to Nb$_{75}$O$_{76}$H$_2$; or mixtures thereof.

10. The method according to claim 2, wherein the photochromic bronze is photochromic tungsten bronze, ranging in various stoichiometric forms from W$_3$O$_9$H$_2$ to W$_{75}$O$_{201}$H$_2$; or photochromic molybdenum bronze, ranging in various stoichiometric forms from Mo$_3$O$_9$H$_2$ to Mo$_{75}$O$_{201}$H$_2$.

11. The method according to claim 1, wherein the matrix comprises unpolished Corning code 7930 porous Vycor glass or tetramethoxysilane/methanol/water xerogel.

12. The method according to claim 11, wherein the tetramethoxy-silane/methanol/water xerogel has been dried at about 180° C. to about 200° C.

13. The method of claim 1 wherein the photochromic metal oxide entity is formed in the matrix by exposing a monometallic carbonyl precursor of the photochromic metal oxide entity to ultraviolet light.

14. The method of claim 13 wherein the monometallic carbonyl precursor is W(CO)$_6$, Mo(CO)$_6$, Fe$_3$(CO)$_{12}$, or mixtures thereof.

* * * * *